United States Patent
Steinbüchel et al.

(10) Patent No.: US 10,889,839 B2
(45) Date of Patent: Jan. 12, 2021

(54) BIOSYNTHETIC ORGANISMS WITH ENHANCED CARBON UTILIZATION

(71) Applicant: INVISTA NORTH AMERICA S.A.R.L., Wilmington, DE (US)

(72) Inventors: Alexander Steinbüchel, Redcar (GB); Jessica Eggers, Redcar (GB); Alexander Brett Foster, Redcar (GB); Jonathan Kennedy, Redcar (GB)

(73) Assignee: INVISTA North America S.a.r.l., Wilmington, DE (US)

( * ) Notice: Subject to any disclaimer, the term of this patent is extended or adjusted under 35 U.S.C. 154(b) by 0 days.

(21) Appl. No.: 16/685,290

(22) Filed: Nov. 15, 2019

(65) Prior Publication Data

US 2020/0157582 A1 May 21, 2020

Related U.S. Application Data

(60) Provisional application No. 62/768,349, filed on Nov. 16, 2018.

(51) Int. Cl.
*C12P 7/16* (2006.01)
*C12R 1/01* (2006.01)
*C12N 1/20* (2006.01)

(52) U.S. Cl.
CPC ............... *C12P 7/16* (2013.01); *C12N 1/20* (2013.01); *C12R 1/01* (2013.01)

(58) Field of Classification Search
CPC ........................................................ C12P 7/16
See application file for complete search history.

(56) References Cited

U.S. PATENT DOCUMENTS

2018/0100160 A1   4/2018  Bawdon et al.

OTHER PUBLICATIONS

Schwartz, E. et al., "A proteomic view of the facultatively chemolithoautotrophic lifestyle of Ralstonia eutropha H16", Proteomics, vol. 9, 2009, pp. 5132-5142.

Weihs, V. et al., "The formation of an oxygen-binding flavohemoprotein in Alcaligenes eutrophus is plasmid-determined", Archives of Microbiology, vol. 151, 1989, pp. 546-550.

Pilhofer, M. et al., "Characterization of bacterial operons consisting of two tubulins and a kinesin-like gene by the novel Two-Step Gene Walking method", Nucleic Acids Research, vol. 35, No. 20, Oct. 16, 2007, pp. 1-8.

Friedrich, C.G. et al., "Formation of Enzymes of Autotrophic Metabolism During Heterotrophic Growth of Alcaligenes eutrophus", Journal of General Microbiology, vol. 122, 1981, pp. 69-78.

Lorenzo, V.D. et al., "[31] Analysis and Construction of Stable Phenotypes in Gram-Negative Bacteria with Tn5- and Tn10-Derived Minitransposons", Methods in Enzymology, vol. 235, 1994, pp. 386-405.

Sillman, C.E. et al., "Isolation of nonobligate bacterial predators of bacteria from soil1", Canadian Journal of Microbiology, vol. 32, No. 9, 1986, pp. 760-762.

Byrd, J.J. et al., "Bacterial control of Agromyces ramosus in soil", Canadian Journal of Microbiology, vol. 31, 1985, pp. 1157-1163.

Zeph, L.R. et al., "Gram-Negative Versus Gram-Positive (Actinomycete) Nonobligate Bacterial Predators of Bacteria in Soilt", Applied and Environmental Microbiology, vol. 52, No. 4, Oct. 1986, pp. 819-823.

Makkar, N.S. et al., "*Cupriavidus necator* gen. nov., sp. nov.: a Nonobligate Bacterial Predator of Bacteria in Soil", Applied and Environmental Microbiology, vol. 37, No. 4, Oct. 1987, pp. 323-326.

Bowien, B. et al., "Genetics and control of CO2 assimilation in the chemoautotroph Ralstonia eutropha", Archives of Microbiology, vol. 178, No. 2, Aug. 2002, pp. 85-93.

Srivastava, S. et al., "Mutagenesis of Alcaligenes eutrophus by Insertion of the Drug-Resistance Transposon Tn5", Archives of Microbiology, vol. 131, 1982, pp. 203-207.

*Primary Examiner* — Tekchand Saidha
(74) *Attorney, Agent, or Firm* — Invista North America S.A.R.L.

(57) ABSTRACT

Nonnaturally occurring organisms exhibiting improved carbon utilization and methods for production and use of these nonnaturally occurring organisms in chemical production from carbon containing feedstocks are provided.

10 Claims, 2 Drawing Sheets

BIOSYNTHETIC ORGANISMS WITH ENHANCED CARBON UTILIZATION

This patent application claims the benefit of priority from U.S. Provisional Application Ser. No. 62/768,349, filed Nov. 16, 2018, the contents of which is herein incorporated by reference in its entirety.

FIELD

The invention relates to biosynthetic, nonnaturally occurring organisms exhibiting improved carbon utilization, methods for their production, and methods for their use in chemical production.

BACKGROUND

Microbial conversion of bioderived feedstocks to commercially valuable chemicals offers the potential for lower cost routes to these products. Some of these commercially valuable chemicals include, but are not limited to, polyhydroxyalkanoates (PHAs), nylon intermediates such as caprolactam, adipic acid, 1,6-hexamethylene diamine, butanediols such as 1,4-butanediol, 1,3-butanediol, and 2,3-butanediol, butanols such as 1-butanol and 2-butanol, succinic acid, butadiene, isoprene, and 3-hydroxypropanoic acid.

Many microbial processes rely on carbohydrates such as sucrose or glucose as the preferred feedstock. It is advantageous, however, to utilize an alternative lower cost feedstock such as, but not limited to, a polyol such as glycerol, syngas or fatty acids. Glycerol, for example, accumulates in large amounts as a by-product of biodiesel production and is therefore available at low prices.

Fixation of inorganic carbon into biomass in autotrophic organisms such as plants and microorganisms is one of nature's predominant biochemical processes, supplying the carbon building blocks necessary to sustain life. In addition, biological carbon fixation represents a means to generate biofuels or other chemical commodities utilizing renewable solar energy. Autotrophic genes i.e. soluble hydrogenases (SH) and cbb genes are expressed when a host organism is grown on glycerol (Friedrich et al. Journal of General Microbiology 1981 122:69-78 and Schwartz et al. Proteomics 2009 9:5132-5142). In contrast, these SH and cbb genes are not expressed when the same host is grown on other organic substrates such as pyruvate or fructose.

There is a need for methods and organisms with improved carbon utilization to produce chemicals or intermediates.

SUMMARY

An aspect of the present invention relates to biosynthetic, nonnaturally occurring organisms modified to exhibit enhanced, improved carbon utilization. In one nonlimiting embodiment, the organism modified in accordance with the present invention is capable of expressing ribulose-1,5-bisphosphate carboxylase/oxygenase (RuBisCo) carbon fixation genes.

In one nonlimiting embodiment, the nonnaturally occurring organism comprises a disruption in its cbbX gene leading to improved carbon utilization.

In one nonlimiting embodiment, the nonnaturally occurring organism comprises a disruption in another cbb or cbb-like gene yielding a similar phenotype to the cbbX disruption.

In one nonlimiting embodiment, the nonnaturally occurring organism is a mutant C. necator species.

In one nonlimiting embodiment, the nonnaturally occurring organism exhibits improved growth on a feedstock comprising a polyol.

In one nonlimiting embodiment, the nonnaturally occurring organism exhibits improved growth on a feedstock comprising glycerol.

Another aspect of the present invention relates to a method for production of a nonnaturally occurring organism which exhibits improved carbon utilization.

In one nonlimiting embodiment, the organism modified in accordance with the present invention is capable of expressing RuBisCo carbon fixation genes.

In one nonlimiting embodiment, the method comprises introducing a disruption into a cbbX gene of the organism leading to improved carbon utilization.

In one nonlimiting embodiment, the method comprises introducing a disruption in another cbb or cbb-like gene yielding a similar phenotype to the cbbX disruption.

Yet another aspect of the present invention relates to a method for use of these nonnaturally occurring organisms in chemical production from a carbon containing feedstock.

DETAILED DESCRIPTION

Figure 1:
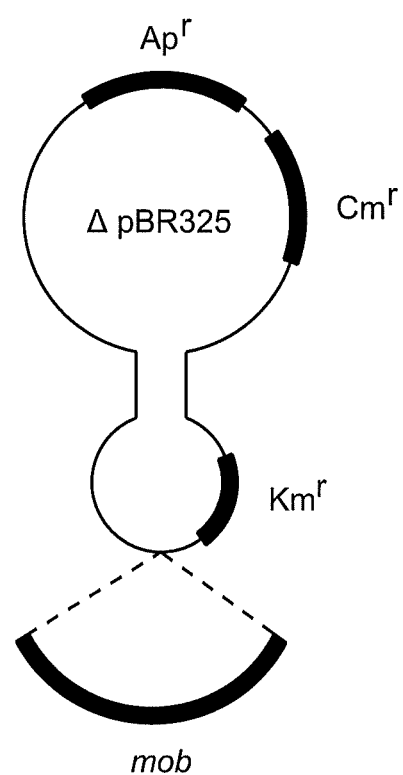
FIG. 1 is a schematic structure of plasmid pSUP5011 including a gene required for plasmid mobilization (mob), an ampicillin resistance cassette (Apr), a chloramphenicol resistance cassette (Cmr), and a kanamycin resistance cassette (Kmr).

The present invention provides nonnaturally occurring organisms which exhibit increased carbon utilization as well as methods for their production and use to produce chemicals.

By "nonnaturally occurring organism" it is meant an organism which has been altered or modified from its natural state.

In one nonlimiting embodiment, the nonnaturally occurring organism has been altered to increase carbon utilization as compared to carbon utilization of the organism in its natural state. In one nonlimiting embodiment, the nonnaturally occurring organism has been altered to increase polyol utilization as compared to polyol utilization of the organism in its natural state. In one nonlimiting embodiment, the nonnaturally occurring organism has been altered to increase glycerol utilization as compared to glycerol utilization of the organism in its natural state.

By "improved" or "increased" carbon, polyol and/or glycerol utilization for purposes of the present invention, it is meant to include a nonnaturally occurring organism which fixes carbon at a higher rate due to, for example, a change in regulation of RuBisCo and/or a nonnaturally occurring organism which utilizes more carbon, polyol and/or glycerol to improve growth as compared to the organism in its natural state.

The cbb-cluster encodes enzymes responsible for $CO_2$ fixation. While the exact function of the gene cbbXp is not known, it is annotated as an AAA+ class of chaperone-like ATPases that is putatively involved in RuBisCO accessory. A homologous cbb-cluster including cbbX (cbbXc) is also present on chromosome 2 of R. eutropha. It is known that deletion of cbbXc results in a loss of autotrophy of *R. eutropha* (Bowien, B. & Kusian, B. Arch Microbiol 2002 178:85-93).

In the present invention, disruption of one or both cbbX genes of an organism is expected to increased carbon utilization by the modified organism.

Organisms altered or modified in accordance with the present invention are preferably capable of expressing RuBisCo carbon fixation genes.

*Cupriavidus necator* is an $H_2$-oxidising, facultative chemolithoautotroph. In the absence of organic substrates, the organism can grow lithoautotrophically on $H_2$ as the sole energy source, fixing $CO_2$ via the Calvin-Benson Bassham cycle. The *Cupriavidus necator* genome consists of three circular replicons; chromosome 1, chromosome 2 and a megaplasmid pHG. The Calvin-Benson Bassham cycle is the main pathway for carbon fixation when *C. necator* is grown under $CO_2/H_2$. Key genes associated with the Calvin-Benson cycle include, but are not limited to, cbbS and cbbL, which encode the small and large subunits of key enzyme RuBisCO, respectively.

Accordingly, in one nonlimiting embodiment, the nonnaturally occurring organism is a mutant *C. necator* or *R. eutropha* species or an organism with properties similar thereto. *C. necator* (previously called *Hydrogenomonas eutrophus, Alcaligenes eutropha, Ralstonia eutropha*, and *Wautersia eutropha*) is a Gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. Additional properties of *C. necator* include microaerophilicity, copper resistance (Makkar & Casida, Int. J. of Systematic Bacteriology 1987 37(4): 323-326), bacterial predation (Byrd et al. Can J Microbiol 1985 31:1157-1163; Sillman & Casida, Can J Microbiol 1986 32:760-762; Zeph & Casida, Applied and Environmental Microbiology 1986 52(4):819-823) and polyhydroxybutyrate (PHB) synthesis. In addition, the cells have been reported to be capable of both aerobic and nitrate dependent anaerobic growth. A nonlimiting example of a *C. necator* organism useful in the present invention is a *C. necator* of the H16 or H39 strain. In one nonlimiting embodiment, a *C. necator* host of the H16 strain with at least a portion of the phaC1AB1 gene locus knocked out (ΔphaCAB), as described in U.S. patent application Ser. No. 15/717,216, teachings of which are incorporated herein by reference, is used. The organism may be selected from non-pathogenic members of the genera *Ralstonia, Wautersia, Cupriavidus, Alcaligenes, Burkholderia* or *Pandoraea*. In one nonlimiting embodiment, the nonnaturally occurring organism is a mutant *C. necator* HF39 species.

In one nonlimiting embodiment, the nonnaturally occurring organism comprises a disruption in a cbbX gene leading to improved carbon utilization. In one nonlimiting embodiment, the nonnaturally occurring organism comprises a disruption of the cbbXp gene of the $CO_2$ fixation cbb-cluster in the megaplasmid pHG of *C. necator*. In one nonlimiting embodiment, the nonnaturally occurring organism lacks one or both cbbX genes.

In one nonlimiting embodiment, the nonnaturally occurring organism comprises a disruption in another cbb or cbb-like gene yielding a similar phenotype to the cbbX disruption.

It is known that when *Cupriavidus necator* H16 is grown on glycerol, key enzymes of autotrophic energy generation such as hydrogenases and $CO_2$ fixation are expressed (Friedrich et al. Journal of General Microbiology 1981 122:69-78 and Schwartz et al. Proteomics 2009 9:5132-5142). In fact, when grown in glycerol these enzymes were formed at activities comparable with those found under autotrophic growth conditions with $H_2$ and $CO_2$ as sources of energy and carbon.

The inventors herein have now identified a nonnaturally occurring *C. necator* organism showing improved growth on a glycerol-based substrate. Determination of the genotype of nonnaturally occurring organism revealed a disruption of the cbbXp gene in the megaplasmid pHG of *Cupriavidus necator*.

Also provided by the present invention are methods for production of a nonnaturally occurring organism which exhibits increased carbon utilization.

In one nonlimiting embodiment, the method comprises introducing a disruption into one or both cbbX genes of the organism leading to improved carbon utilization. In one nonlimiting embodiment, the method comprises introducing a disruption in another cbb or cbb-like genes yielding a similar phenotype to the cbbX disruption. Various methods for introducing a disruption in a gene are well known and can be used in the present invention.

In one nonlimiting embodiment, the nonnaturally occurring organism is a mutant *C. necator* or *R. eutropha* species or an organism with properties similar thereto as described herein.

In addition, the present invention provides methods for chemical production using these nonnaturally occurring organisms. In these methods, the nonnaturally occurring organism is grown on a carbon based feedstock under conditions which promote production of a selected chemical. Examples of carbon based feed stocks include, but are not limited to, feed stocks comprising polyols such as glycerol, syngas and/or fatty acids. Examples of selected chemicals produced in accordance with these methods include, but are not limited to, polyhydroxyalkanoates (PHA), nylon intermediates, butanediols, butanols, succinic acid, butadienes, isoprene, and 3-hydroxypropanoic acid.

In addition, the present invention provides bio-derived, bio-based, or fermentation-derived products produced using the methods and/or nonnaturally occurring organisms disclosed herein. Examples of such products include, but are not limited to, compositions comprising at least one bio-derived, bio-based, or fermentation-derived compound or any combination thereof, as well as polymers, plastics, molded substances, formulations and semi-solid or non-semi-solid streams comprising one or more of the bio-derived, bio-based, or fermentation-derived compounds or compositions, combinations or products thereof.

Although specific advantages have been enumerated above, various embodiments may include some, none, or all of the enumerated advantages. Further, other technical advantages may become readily apparent to one of ordinary skill in the art after review of the description herein. It should be understood at the outset that, although exemplary embodiments are described herein, the principles of the present disclosure may be implemented using any number of techniques, whether currently known or not. The present disclosure should in no way be limited to the exemplary implementations and techniques described herein.

Modifications, additions, or omissions may be made to the compositions, systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

The following section provides further illustration of the methods and materials of the present invention. The Example is illustrative only and is not intended to limit the scope of the invention in any way.

EXAMPLE

Example 1: Tn5 Mutagenesis

Tn5 mutagenesis, as described for example by de Lorenzo and Timmis (Methods in Enzymology 1994 235:386-405) was performed to identify essential genes for glycerol utilization in *C. necator*. The plasmid pSUP5011 (FIG. 1) was used to generate Tn5 mutants of *R. eutropha* HF39 (DSM 15444), a *R. eutropha* strain that is resistant to higher concentrations of streptomycin (Srivastava et al., Arch, Microbiol. 1982 131:203-207). Mutants were transferred to solid MSM (mineral salts medium) with 1% (v/v) glycerol and screened for enhanced or reduced growth on glycerol in comparison to the wildtype. Plates were incubated at 30° C. and colony-formation was checked every day. If colonies were growing faster or slower in comparison to the wildtype or the other colonies, they were transferred again and cultivated also in liquid MSM with glycerol as sole carbon source.

Out of 2,600 mutants, one showed a clear glycerol negative phenotype. The mutant has a disruption of a gene coding for a predicted P-loop containing kinase (locus tag H16_A0381).

In addition, two Tn5 mutants showed improved growth on solid MSM with 1% (v/v) glycerol.

Figure 2:
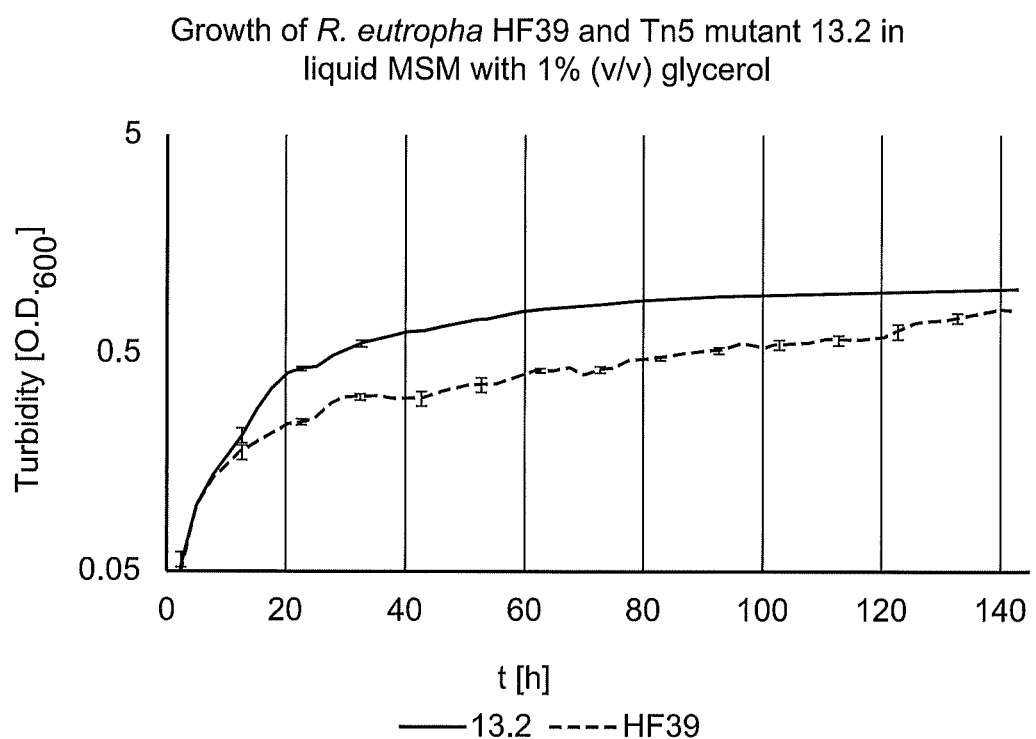
FIG. 2 is a graph showing growth behavior of R. eutropha HF 39 and the mutant R. eutropha HF39 Tn5 13.2 in mineral salts medium (MSM) with 1% (v/v) glycerol (semi-logarithmic scale).

The growth behavior of one of these mutants (*R. eutropha* HF39 Tn5 13.2) was further analyzed in liquid MSM with 1% (v/v) glycerol in comparison to the parent strain *R. eutropha* HF39 and it showed enhanced growth during exponential phase (See FIG. 2).

Determination of the genotype using the two step gene walking method (Pilhofer et al. Nucleic Acids Res. 2007 35) revealed a disruption of the cbbXp gene of the cbb-cluster in the megaplasmid pHG of *R. eutropha*.

What is claimed is:

1. A nonnaturally occurring organism which exhibits increased carbon utilization, said nonnaturally occurring organism being a *Cupriavidus* species and comprising disruption in a one or more cbbX genes leading to increased carbon utilization as compared to an organism without the disruption.

2. The nonnaturally occurring organism of claim 1 wherein the nonnaturally occurring organism is a mutant *Cupriavidus necator* species.

3. The nonnaturally occurring organism of claim 1 which exhibits increased polyol utilization.

4. The nonnaturally occurring organism of claim 1 which exhibits increased glycerol utilization.

5. A method for production of a nonnaturally occurring organism of a *Cupriavidus* species which exhibits increased carbon utilization, said method comprising introducing disruption into a one or more cbbX genes of the organism leading to improved carbon utilization as compared to an organism without disruption.

6. The method of claim 5 wherein the nonnaturally occurring organism is a mutant *Cupriavidus necator* species.

7. The method of claim 5 wherein the nonnaturally occurring organism exhibits increased polyol utilization.

8. The method of claim 5 wherein the nonnaturally occurring organism exhibits increased glycerol utilization.

9. A method for producing a chemical from a carbon containing feedstock, said method comprising contacting the feedstock with the nonnaturally occurring organism of claim 1.

10. The method of claim 9 wherein the produced chemical is selected from a polyhydroxyalkanoates (PHA), a nylon intermediate, a butanediol, a butanol, succinic acid, butadiene, isoprene, and 3-hydroxypropanoic acid.

* * * * *